United States Patent [19]

Klieman et al.

[11] 4,452,357

[45] Jun. 5, 1984

[54] SURGICAL STAPLER

[75] Inventors: Charles H. Klieman, 3737 Century Blvd., Lynwood, Calif. 90262; Richard M. Densmore, South Gate, Calif.

[73] Assignees: Charles H. Klieman, Lynwood; L. David Covell, Los Angeles, both of Calif. ; a part interest

[21] Appl. No.: 483,746

[22] Filed: Apr. 14, 1983

Related U.S. Application Data

[63] Continuation of Ser. No. 171,129, Jul. 22, 1980, abandoned.

[51] Int. Cl.³ ............................................ B65D 85/24
[52] U.S. Cl. .................................... 206/339; 128/325
[58] Field of Search ............... 206/339, 355, 357, 359, 206/360; 72/407; 227/19; 128/325

[56] References Cited

U.S. PATENT DOCUMENTS 2,307,384  1/1943  Bowen ................................ 206/339

FOREIGN PATENT DOCUMENTS

1321408  6/1973  United Kingdom ................ 206/339

Primary Examiner—Joseph Man-Fu Moy
Attorney, Agent, or Firm—Spensley, Horn, Jubas & Lubitz

[57] ABSTRACT

A hemostatic clip applicator useful in the rapid and automatic application of hemostatic clips for the strangulation of tubular members is disclosed. The applicator consists of a main body, a clip magazine externally attached to the main body, clip deforming jaws attached to one end of the main body, clip feed means located within the main body and actuating means attached to the feed means and deforming jaws. In operation, one of many hemostatic clips stored in the clip magazine is fed into the main body and guided to the deforming jaws by the interaction of the actuating means and the feed means. When the clip is properly located about a tubular member, further actuation of the actuating means results in the deformation of the clip about the tubular member. Upon further activation of the actuating means, the sequential process of feeding a clip from the magazine and deforming the clip about other tubular members may be rapidly repeated until the supply of clips in the magazine is depleted.

9 Claims, 20 Drawing Figures

SURGICAL STAPLER

This is a continuation of application Ser. No. 171,129, filed on July 22, 1980, now abandoned.

BACKGROUND OF THE INVENTION

1. Copending Patent Applications

In copending U.S. patent application Ser. No. 822,076 entitled HEMOSTATIC CLIP APPLICATOR filed Aug. 5, 1977, and assigned to the present assignee, a hemostatic clip applicator for the stangulation of tubular members in a rapid and automatic manner is disclosed. Also, in copending U.S. patent application Ser. No. 822,095 entitled HEMOSTATIC CLIP filed Aug. 5, 1977 now U.S. Pat. No. 4,188,953, and assigned to the present assignee, hemostatic clips adapted for utilization in the present invention and similar devices is disclosed.

2. Field of the Invention

The invention relates to the field of devices useful in the application of hemostatic clips, and more specifically, to devices for the application of hemostatic clips used in the strangulation of blood vessels and other fluid ducts.

3. Prior Art

In a typical surgery procedure, a great many veins, arteries, and other blood vessels must be severed and closed. This is often a difficult and time consuming procedure since many vessels are located in obscure areas where there is little room in which to work. Thus, it is apparent that a device which would reduce the time requied for closure of blood vessels would be of great benefit to both the surgeon and the patient.

One prior art attempt to provide a device which can more rapidly close a blood vessel is disclosed by Wood, U.S. Pat. No. 3,326,216. The Wood device consists of a hemostat-like instrument which has finger loop portions coupled to jaw portions. The jaw portions are adapted to hold a hemostatic clip therebetween so that the clip may be closed about a vessel by bringing the finger loops together. Wood also discloses a separate cartridge which holds a plurality of clips. When the Wood device is to be used, the jaw portions are placed about one clip contained in the cartridge, and the clip is removed from the cartridge by the engagement of the clip by the jaw portions. Then when the clip has been used, a new clip may be placed in the device by returning to the clip cartridge and inserting a new clip. Two problems are apparent with the Wood device. First, the hemostatic clips are not automatically fed into the jaws of the device, but must be individually placed there. This procedure is time consuming and cumbersome. In addition, the Wood device is capable of expanding its jaws wider than the width of a clip contained therein. Thus, a clip may be accidentally dropped from the device causing a great deal of inconvenience and delay.

A second prior art attempt to provide more rapid yet effective strangulation of blood vessels and the like is described by Miles, U.S. Pat. No. 3,082,426. Miles discloses a surgical stapling device which consists of finger loops coupled to a pair of arms which terminate in jaw portions, the jaw portions being adapted to grasp and hold a tubular member. The device also has a magazine for holding a plurality of clips along the length of one arm, and manually operable clip ejector means for placing a clip about the tubular member which is to be closed. In operation, the tubular member is first grasped and held by the jaw portions of the Miles device. The surgeon then places his index finger on a button attached to the clip ejector. By urging the button forward, the clip ejector places a clip about the tubular member. Then, the clip may be deformed about the blood bessel by bringing the pair of finger loops together. An obvious disadvantage of the Miles device is that it is cumbersome, in that the surgeon must manually move a clip between the jaws of the device while holding the device steady so as not to loose the grasp of the tubular member. Also, as the clips are used from the cartridge, the button moves farther forward so that it becomes more and more difficult to reach. Also, this procedure is time consuming in that each individual clip must be manually fed between the jaws of the stapling device. Furthermore, the construction of the Miles device, particularly in the jaw portions, provides poor visibility to the surgeon since the thickness of the device obscures the vessels which are to be closed.

Another prior art attempt to provide rapid application of hemostatic clips is disclosed by DeCarlo, U.S. Pat. No. 3,740,944. DeCarlo discloses a gun-like device for suturing and severing blood vessels in a three stage procedure. First, jaws of the device are closed about the blood vessel by the actuation of the gun-like trigger mechanism. Second, a pair of pushers extend through the device and come forward to crimp a pair of clips, brought from an internal magazine, about the vessel in two spaced locations. Third, a blade comes forward from the device upon further actuation of the gun-like handles and severs the blood vessels between the two clip locations.

The internal clip magazine of the DeCarlo device uses a pair of leaf spring assemblies to index a plurality of pairs of hemostatic clips. The clips are stored in a pair of index guide rails where they are moved forward in unison by opposing leaf spring assemblies. One leaf spring assembly is attached to the moveable main body portion while the opposing leaf spring assembly is affixed to one guide rail. When the gun-like handles are actuated, the leaf spring assembly attached to the main body moves forward and contacts portions of the clips contained within the magazine. Further movement of the main body portion moves individual clips along the index guide rail and ultimately ejects a pair of clips. When a pair of clips has been ejected, the main body portion begins to return to its original static position. During this rearward movement of the main body portion, there is a transference of a pair of clips from the index guide rails to the ejection guide rails. This transference occurs when each leaf spring assembly and its corresponding ramp portions guide a clip from one index guide rail to the ejection guide rail where it is available for loading into the front portion of the instrument.

One problem with the DeCarlo device is that, due to the three stage operation, the device is necessarily bulky. This is a major disadvantage in that many surgical procedures require severence and closure of blood vessels in very limited areas so that a bulky instrument may not be able to reach the required vessel. The bulkiness of the device also creates a further disadvantage in that it produces a lack of visibility for the surgeon. Thus, the very vessel that is to be severed and closed may be obscured since the surgeon may not be able to see around the device. A further disadvantage stems from the fact that the DeCarlo device does not adapt to the application of a single clip, but only applies a pair of clips to the vessel to be closed. In a great many surgical procedures, only the application of one clip is desired while the application of two clips would only complicate the severance procedure.

Accordingly, it is a general object of the present invention to provide an improved hemostatic clip applicator device for the strangulation of blood vessels and the like.

It is another object of the present invention to provide an improved hemostatic clip applicating device which automatically feeds clips to its forward portion and then provides automatic deformation of the clips about blood vessels.

It is yet another object of the present invention to provide an improved hemostatic clip applicator device which provides high visibility to the user.

It is yet another object of the present invention to provide an improved hemostatic clip applicator device which has an externally coupled and replaceable clip cartridge or in the alternative, a disposable hemostatic clip applicator device which has an externally coupled clip cartridge.

It is a still further object of the present invention to provide an improved hemostatic clip applicator device which is incapable of accidentally dropping clips from the device.

SUMMARY OF THE INVENTION

A hemostatic clip applicator device useful for rapidly and automatically applying clips for the strangulation of blood vessels and the like is provided. The device has a clip magazine means coupled to the exterior of a main body, the clip magazine means being adapted to hold a plurality of hemostatic clips. Attached to one end of the main body is a clip deforming means adapted to hold and crimp a hemostatic clip about a blood vessel. Slideably disposed within the main body is a clip feed means which is adapted to move clips from the clip magazine means to the clip deforming means. Coupled to the clip feed means and the clip deforming means are actuating means. By a sequential forward and rearward movement of the actuating means, a hemostatic clip is fed from the clip magazine means into the main body, where it is moved forward to the clip deforming means and there crimped about a blood vessel or the like. This sequence of feeding clips to the clip deforming means and crimping them therein, may be repeated until the plurality of clips located in the clip magazine means is depleted.

The novel features which are believed to be characteristic of the invention, both as to its organization and its method of operation, together with further objects and advantages thereof, will be better understood from the following description in connection with accompanying drawings in which a presently preferred embodiment of the invention is illustrated by way of example. It is to be expressly understood, however, that the drawings are for purposes of illustration and description only and are not intended as a definition of the limits of the invention.

DETAILED DESCRIPTION OF THE INVENTION

A hemostatic clip applicator device is disclosed which is useful in rapidly applying a hemostatic clip about blood vessels and other fluid ducts. The hemostatic clip applicator of the present invention may be used with hemostatic clips such as is described in our co-pending application, Ser. No. 822,095, filed on Aug. 5, 1977 entitled "Hemostatic Clip", or with any other suitably adapted hemostatic clip, now U.S. Pat. No. 4,188,953.

Figures 1, 2, 3, 4:
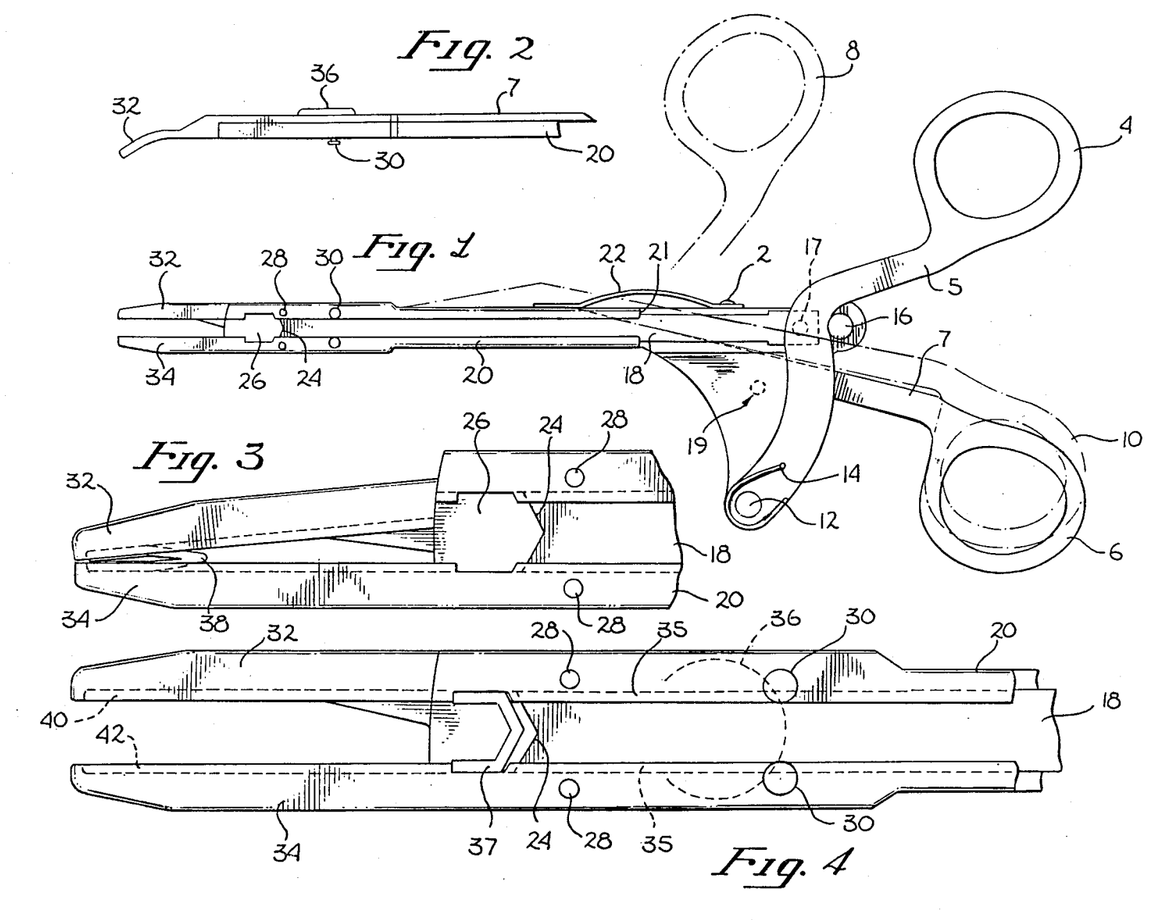
FIG. 1 is a side view of the clip applicating device of the present invention.
FIG. 2 is a top view of the forward portion of the clip applicating device of the present invention, showing the curved jaw portions.
FIG. 3 is an enlarged view of the jaw portions of the present invention showing a hemostatic clip closed by the clip applicating device.
FIG. 4 is an enlarged view of the forward portion of the clip applicating device of the present invention.

Referring to FIG. 1, the hemostatic clip applying device 2 of the present invention is shown in its static configuration. Clip applying device 2 has an actuating means comprised of an upper handle portion and a lower handle portion. In the presently preferred embodiment, the upper handle portion is comprised of upper finger loop 4, and upper finger loop member 5, while the lower handle portion is comprised of lower finger loop 6 and lower finger loop member 7. It can be seen in phantom in FIG. 1 that upper finger loop 4 may be brought to its forward position 8, while lower finger loop 6 may be moved to an inward position 10. Upper finger loop 4 and upper finger loop member 5 pivot about upper finger loop pivot 12 while being biased toward rear stop pin 16 by first spring means 14. Upper finger loop member 5 is coupled to clip feed blade 18 by feed blade pivot 17.

Clip feed blade 18 is a clip feed means which in the presently preferred embodiment is a blade member adapted to slide through main body 20 by the forward movement of upper finger loop 4. Upper finger loop 4 will continue to move clip feed blade 18 through main body 20 until upper finger loop member 5 abuts forward stop means 21. The leading edge 24 of clip feed blade 18 is adapted to correspond to the bail portion or trailing edge of a hemostatic clip which may be placed in recess 26 by any suitably adapted means. In the presently preferred embodiment, leading edge 24 is "V" shaped. Thus, it can be seen from FIG. 1 that when a hemostatic clip is placed in the clip receiving means formed by recess 26, the forward movement of upper finger loop 4 will cause clip feed blade 18 to abut the bail portion of the hemostatic clip and move the clip toward the forward end of main body 20.

Coupled to the forward portion of main body 20 is a clip deforming means adapted to deform a hemostatic clip about a blood vessel or the like. In the presently preferred embodiment, the clip deforming means is comprised of upper jaw portion 32 and lower jaw portion 34. Upper jaw portion 32 is fixedly coupled to lower finger loop member 7 and pivotally coupled to main body 20, while lower jaw portion 34 is fixedly coupled to main body 20. When a hemostatic clip has been fed from the clip magazine into recess 26 and moved forward by clip feed blade 18 to jaw portions 32 and 34, the clip may be squeezed about a blood vessel by first returning upper finger loop 4 to its rearward position and then raising finger loop 6 to its phantom position 10 so that upper jaw portion 32 closes toward lower jaw portion 34. It is important to note that the outward movement of upper jaw portion 32 is limited by the abutment of lower finger loop member 7 with lower finger loop stop pin 19. Thus, if a hemostatic clip is located in jaw portions 32 and 34, it may not be accidentally dropped by the over expansion of upper jaw 32. Lower finger loop 6 and lower finger loop member 7 are biased toward their static configuration by second spring means 22 so that upper jaw portion 32 will return to its open position when lower finger loop 6 is no longer raised to to its phantom position 10. Also shown in FIG. 1 are mounting holes 28 and rivets 30 adapted to couple a clip magazine, which will be more fully described hereinbelow, to main portion 20.

FIG. 2 is a top view of the forward portion of clip applying device 2. Illustrated here is the relationship between main body 20, lower finger loop member 7 and upper jaw portion 32. It can be seen that lower finger loop member 7 is fixedly coupled to upper jaw portion 32, while the combination of member 7 and jaw portion 32 is pivotally coupled to main body 20 by upper jaw pivot 36. Thus, rotation of member 7 about pivot 36 by movement of lower finger loop 6 results in rotation of upper jaw 32 about pivot 36. Therefore, inward and outward movement of lower finger loop 6 will result in movement of upper jaw 32 toward and away from lower jaw portion 34. Also shown in FIG. 2 is the curved configuration of upper jaw portion 32 and lower jaw portion 34. This curved forward portion of clip applying device 2 provides the distinct advantage of improved visability during usage since the vessel which is to be closed will be located to one side or the other of the main body 20. Although the presently preferred embodiment of the upper and lower jaw portions utilizes a curved configuration, other configurations, such as straight jaw portions, may also be used.

FIG. 3 illustrates the jaw portions 32 and 34 as they are closed about a deformed clip 38. This configuration would have resulted from the feeding of a clip into the jaw portions 32 and 34 by the forward movement of upper finger loop 4, followed by the rearward movement of upper finger loop 4 and then the inward movement of lower finger loop 6. It may be noted that rearward movement of upper finger loop 4 has caused feed blade 18 to return to its unactuated position, thus exiting jaw portions 32 and 34 and recess 26, so that the jaw portions are free to close about a clip.

FIG. 4 shows in greater detail the forward portion of clip applying device 2, including clip feed blade 18 and its leading edge 24 as it is disposed in groove 35 in main body 20. It can be seen that a clip 37 disposed in recess 26 will be moved forward by the leading edge 24 of clip feed blade 18 so that the clip 37 and clip feed blade 18 slide within the groove 40 in upper jaw portion 32 and groove 42 in lower jaw portion 34. As noted in FIG. 2, jaw portions 32 and 34 are curved away from main body 20. Thus, feed blade 18 must be configured so as to be capable of being moved forward through grooves 35, 40 and 42 while simultaneously bending away from main body 20 in grooves 40 and 42. In the presently preferred embodiment, this capability has been provided by constructing feed blade 18 of four layers of thin blades of metal in a laminated configuration. The four layers are only coupled at discrete points so that feed blade 18 is able to move longitudinally through main body 20 while curving around grooves 40 and 42 in jaw portions 32 and 34. Also shown in FIG. 4 are rivets 30 and mounting holes 28 for coupling a clip magazine to the clip applicator device 2.

Figure 5:
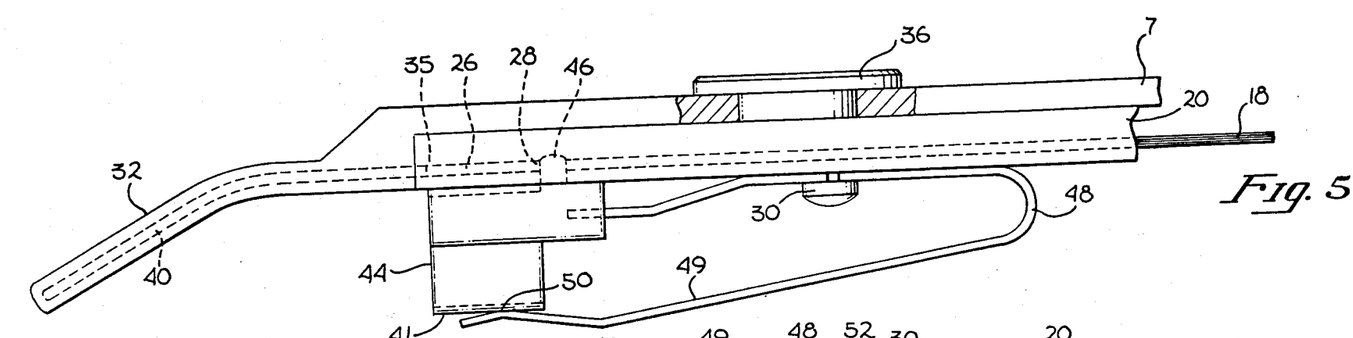
FIG. 5 is an enlarged view of the top of the forward portion of the clip applicating device showing the clip magazine in its relationship to the device.

FIG. 5 is a top view of the forward portion of clip applying device 2 showing lateral clip magazine 41 replaceably coupled to main body 20 by clip magazine pin 46 disposed in mounting hole 20 and clip leaf spring 48 disposed under rivet 30. Hemostatic clips are disposed in clip magazine housing 44 in a lateral relationship to main body 20 and urged toward recess 26 of clip applying device 2 by the spring contact 50 of central clip leaf spring 49. Thus, when clip feed blade 18 is in its fully retracted position, recess 26 is clear so that a clip may be fed from clip magazine housing 44 into recess 26. The clip disposed in recess 26 is then available for movement to the jaw portions 32 and 34 when clip feed blade 18 is moved forward by the actuation of upper finger loop 4. Both the clip and clip feed blade 18 then move through groove 35 in main body 20 and grooves 40 and 42 in upper jaw portions 32 and 34 respectively until upper finger loop member 5 has reached its farthest forward position. Also shown in FIG. 5 is lower finger loop member 7 as it is coupled to upper jaw portion 32, so that they both may rotate about upper jaw pivot 36.

Figures 6, 7:
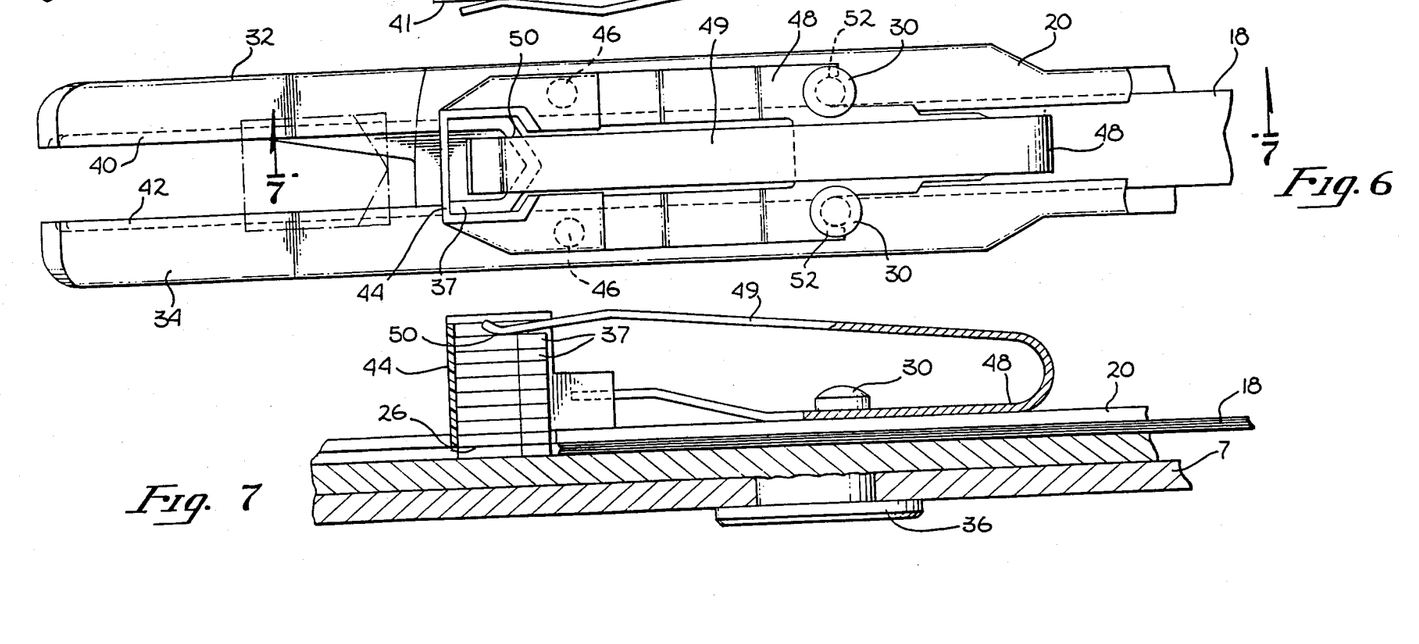
FIG. 6 is an enlarged view of the forward portion of the clip applicating device of the present invention.
FIG. 7 is a side view of the clip magazine of the present invention.

FIG. 6 is a top view of the forward portion of the clip applying device 2, showing the lateral clip magazine housing 44 and its associated clip leaf spring 48. It can be seen from this illustration that clip magazine housing 44 is coupled to main body 20 by a portion of clip leaf spring 48 which lies under rivet 30, and by clip magazine pins 46 being disposed in mounting holes 28 in main body 20. Thus, to mount lateral clip magazine housing 44 on main body 20, recesses 52 in clip leaf spring 48 are urged around the shaft portion of rivet 30 until pins 46 can be located in mounting holes 28. When lateral clip magazine housing 44 is so positioned, central leaf spring 49 is positioned over the clips 37 contained in housing 44 so that leaf spring 49 contacts the clips 37 at point 50 and thereby urges them into the main body 20. When the clips 37 in clip magazine housing 44 have been depleted, magazine 41 may be removed and a new magazine installed by lifting housing 44 from main body 20 until pins 46 have cleared holes 28 so that clip leaf spring 44 may be moved longitudinally out from under rivets 30. When the depleted magazine 44 has been removed, a new magazine containing a supply of clips 37 may be installed.

FIG. 7 is a side cutaway view showing in greater detail lateral clip magazine 41. Clip leaf spring 48 is disposed under rivet 30 so that central clip leaf spring 49 is positioned over clips 37 contained in magaine housing 44. It can be seen from this figure that central leaf spring 49 exerts a pressure on clips 37 at contact point 50 so as to urge the clips individually into recess 26 of main body 20. When clip feed blade 18 is in its fully retracted position, recess 26 is empty so that a clip 37 may move into recess 26 and be held there by the urging of adjacent clips 37. When a clip 37 is to be moved to the jaw portions 32 and 34 of clip applying device 2, clip feed blade 18 then slides laterally through body portion 20 and carries clip 37 from recess 26 toward the jaw portions 32 and 34.

Figures 8, 10:
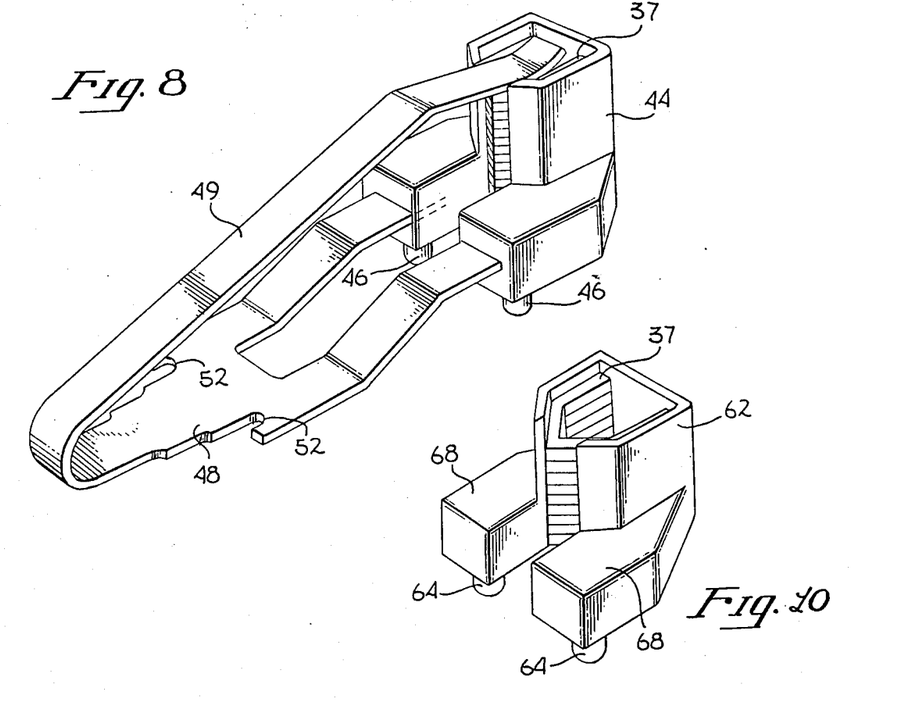
FIG. 8 is a perspective view of the clip magazine of the present invention.
FIG. 10 is a perspective view of an alternate embodiment of the clip magazine of the present invention.

FIG. 8 is a perspective view of lateral clip magazine 41, with its associated clip leaf spring 48, central clip leaf spring 49 and housing 44. Disposed in housing 44 are a plurality of hemostatic clips 37. Central clip leaf spring 49 is positioned so as to urge hemostatic clips 37 to exit from housing 44 through the bottom thereof. Also illustrated in FIG. 8 are the mounting means for magazine housing 44, including pins 46, and recesses 52 disposed in clip leaf spring 48.

It can be seen from the above description and particularly FIGS. 1, 5 and 8 that clip applicating device 2 of the present invention provides an automatic feeding and crimping of hemostatic clips. By simply moving upper and lower finger loops 4 and 6 outwardly and then inwardly, a clip is moved from an external magazine 41, into a receiving means 26, and disposed in jaw portions 32 and 34 where it is deformed around a blood vessel or the like. This process of inward and outward movement of finger loops 4 and 6 may be repeated rapidly, so that one vessel after another is closed by the hemostatic clips 37, until the supply of clips in magazine 41 is depleted. At this point a new magazine 41 may be substituted for the depleted magazine so that vessel closures may be continued.

The clip applicating device 2 of the present invention provides the further advantage of high visability to the user. Because the device 2 is of an extremely thin design, essentially the width of currently used hemostats and because jaw portions 32 and 34 are curved away from the main body 20, a surgeon using clip applying device 2 will have a clear view of the vessel he is closing and, in addition, will be able to reach remote and obscure regions for further vessel closure. In addition, clip applying device 2 is constructed so as to prevent a clip 37 from accidentally dropping from the device, thereby obivating a great deal of inconvenience and lost time.

Figure 9:
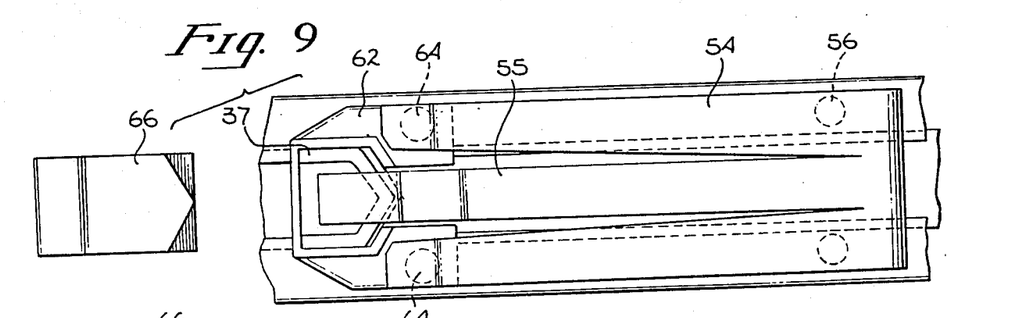
FIG. 9 is a top view of an alternate embodiment of the clip magazine means of the present invention.

FIG. 9 illustrates an alternate embodiment of a clip magazine which may be externally coupled to clip applying device 2. In this embodiment, a main body spring 54 is permanently coupled to clip applying device 2 by rivets 56. The main body spring 54 is adapted to hold clip housing 62 in its proper alignment with main body 20 in conjunction with housing pins 64. Main body spring 54 includes a central body spring 55 adapted to rest upon the clips 37 disposed in clip housing 62. FIG. 9 also illustrates a top view of protective cover 66 which is removed from clip housing 62 when housing 62 is to be utilized. Protective cover 66 prevents clips 37 from becoming dislodged from clip housing 62 until housing 62 is placed properly in its relationship to main body 20.

Figure 11:
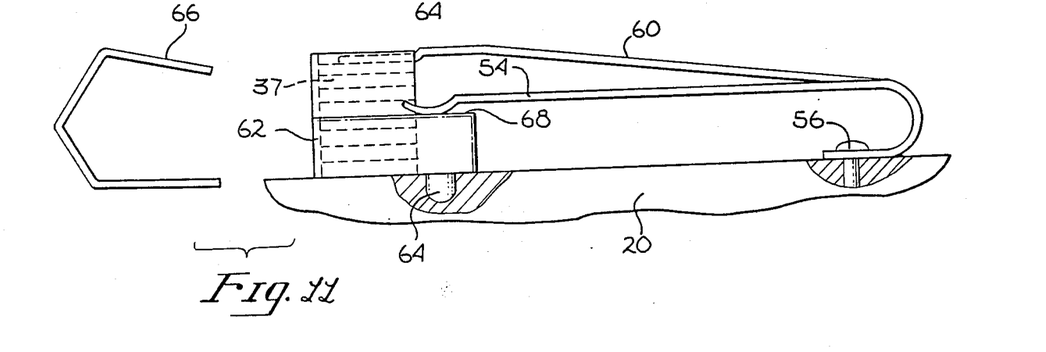
FIG. 11 is a side view of an alternate embodiment of the clip magazine and clip magazine spring means of the present invention.

FIGS. 10 and 11 further illustrate the alternate embodiment of a clip magazine. FIG. 10 is a perspective view of clip housing 62 showing a plurality of hemostatic clips 37 disposed therein. Clip housing 62 includes housing shoulders 68 and housing pins 64. FIG. 11 is a side view of clip housing 62 as it is held in place against main body 20 by housing leaf spring 58 resting on shoulders 68. Main body spring 54 is coupled to the main body 20 by rivet 56 so that main body spring portions 54 rest agaiint shoulders 68 of clip housing 62 while clip leaf spring 60 rests against the upper most hemostatic clip 37.

Figure 12:
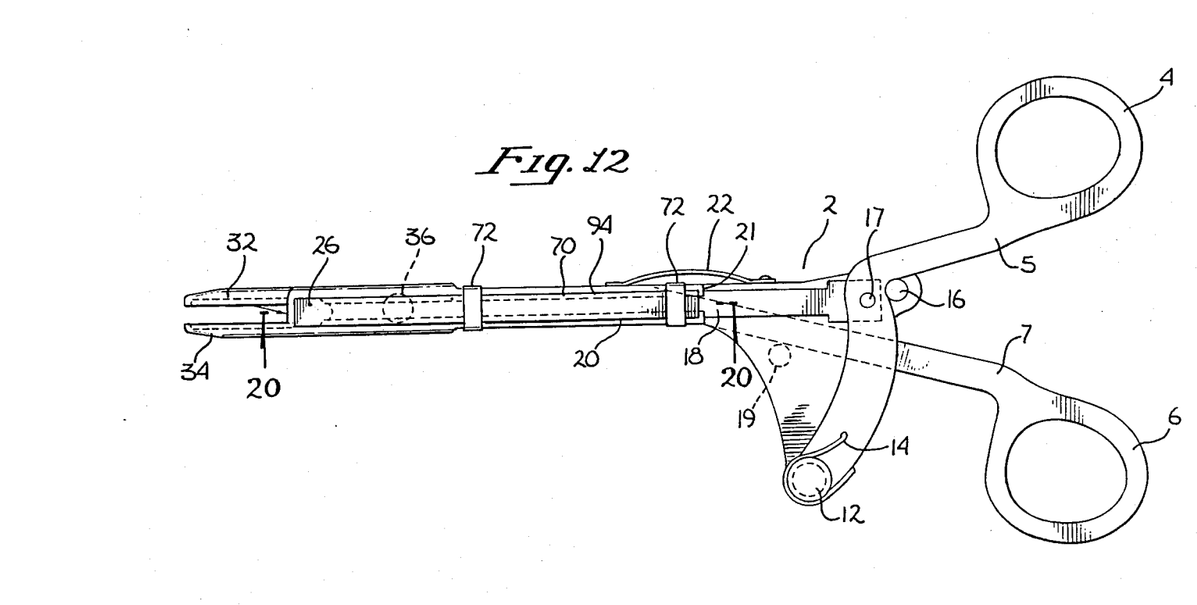
FIG. 12 is a side view of an alternate embodiment of the clip applicating device of the present invention.

FIG. 12 illustrates clip applying device 2 which utilizes another alternate embodiment of a clip magazine, in this case a parallel clip magazine 70. Disposed in parallel clip magazine 70 is a plurality of hemostatic clips which lay parallel to main body 20 and are sequentially fed toward recess 26. Parallel clip magazine 70 is replaceably coupled to main body 20 by magazine couplings 72, which in the presently preferred embodiment are spring clips which snap over corresponding portions of main body 20. The magazine 70 is so adapted that forward movement of upper finger loop 4 and the corresponding movement of upper finger loop member 5 and clip feed blade 18 results in the sequential placement of hemostatic clips in recess 26. Further actuation of upper finger loop 4 results in movement of a clip between upper jaw portion 32 and lower jaw portion 34. When a clip has been so placed, upper finger loop 4 is returned until it abuts rear stop pin 16 at which time lower finger loop 6 may be moved inward so as to cause upper jaw portion 32 to move toward lower jaw portion 34 and thereby close the hemostatic clip about the blood vessel. Upper finger loop 4 is biased toward stop pin 16 by first spring 14, while lower finger loop 6 is biased toward lower finger loop member stop pin 19 by second spring means 22.

Figure 13:
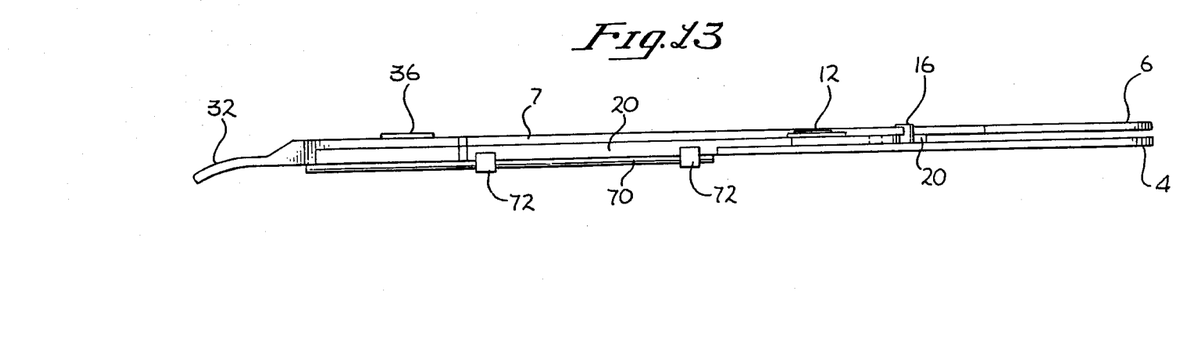
FIG. 13 is a top view of an alternate embodiment of the clip applicating device of the present invention.

FIG. 13 is a top view of clip applying device 2 showing parallel clip magazine 70 and its coupling 72 to main body 20. Also shown in FIG. 13 is the relationship between upper finger loop 4, lower finger loop 6, and lower finger loop member 7 as it is coupled to upper jaw portion 32. Lower finger loop member 7 is fixedly coupled to upper jaw portion 32, while lower finger loop member 7 is pivotally coupled to main body 20 by upper jaw pivot 36. Thus, movement of lower finger loop 6 results in movement of upper jaw portion 32 about upper jaw pivot 36. It can be seen from FIGS. 12 and 13 that parallel clip magazine 70 provides even greater visability to the surgeon since the magazine 70 only slightly increases the width of the clip applying device 2.

Figure 14:
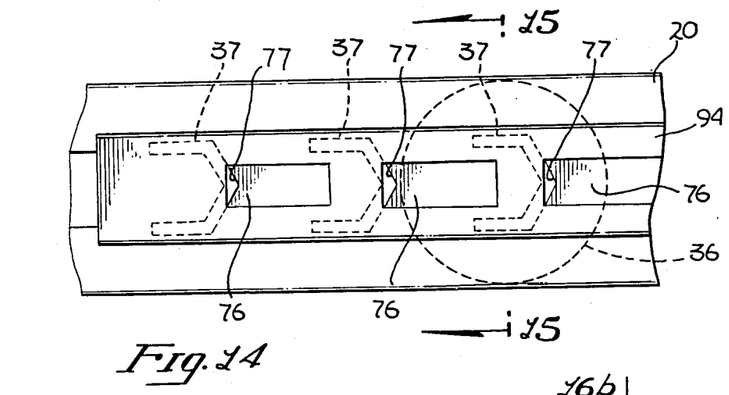
FIG. 14 is an enlarged view of a portion of the clip magazine means.

FIGS. 14, 15, 16 and 17 generally illustrate that parallel clip magazine 70 is comprised of a parallel clip magazine housing 94, which has a plurality of inwardly biased leaf springs 76, a lost motion link 82 and a clip loading blade 78 which also has a plurality of inwardly biased leaf springs 88. More specifically, FIG. 14 illustrates leaf springs 76 in clip housing 94 and the configuration of hemostatic clip 37 within housing 94. It can be seen that each leaf spring 76 has a "V" shaped leading edge 77 which is adapted to correspond to the "V"

shaped bail portion of clips 37. As will be discribed more fully hereinbelow, the function of each leaf spring 76 is to prevent rearward movement of clips 37.

Figure 15:
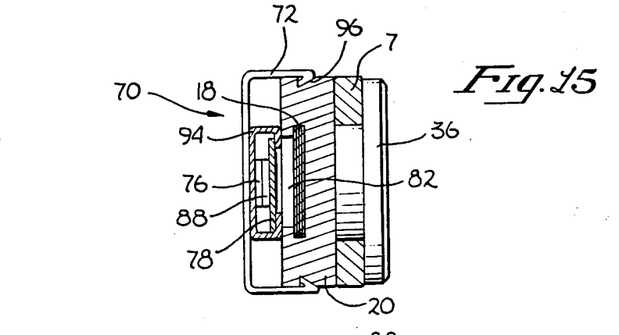
FIG. 15 is a cross-sectional view of the applicating device of the present invention takes along lines 15—15 of FIG. 14.
Figures 16A, 16B:
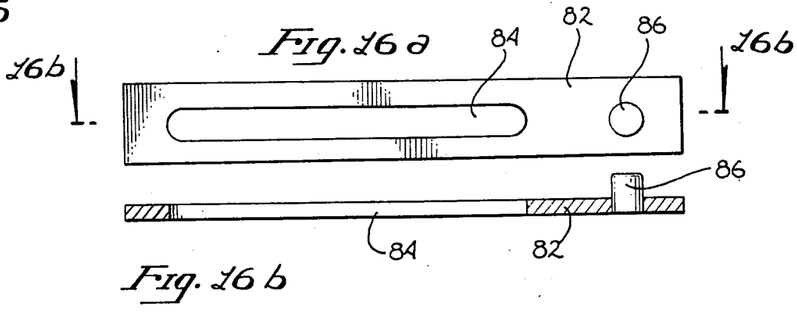
FIGS. 16a and 16b are a top and side view respectively of the lost motion link means of the present invention.

FIG. 15 is a cross-sectional view of magazine 70 as it is coupled to main body 20 by magazine couplings 72. Magazine coupling 72 is adapted to spring outward around main body 20 until it can be positioned in notch 96 in main body 20. Disposed within parallel clip magazine 70 are inwardly biased leaf springs 76 in housing 94, clip loading blade 78, with inwardly biased leaf springs 88, along with lost motion link 82. Adjacent lost motion link 82 is clip feed blade 18 of clip applying device 2. FIGS. 16a and 16b show in greater detail lost motion link 82. FIG. 16a, a top view of lost motion link 82, illustrates lost motion link pin 86 and slot 84. FIG. 16b is a side view of lost motion link 82 also illustrating pin 86 and slot 84. Pin 86 is fixedly coupled to one end of lost motion link 82, while slot 84 is an elongated aperture disposed entirely through link 82.

Figure 17A:
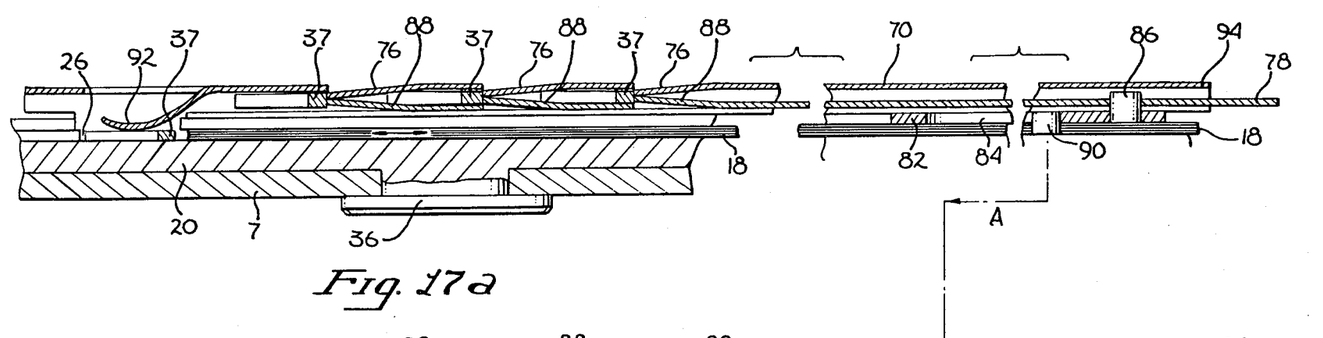
FIGS. 17a, 17b and 17c illustrate the progressive movement of a clip within the clip magazine means of an alternate embodiment of the present invention.
Figure 17B:
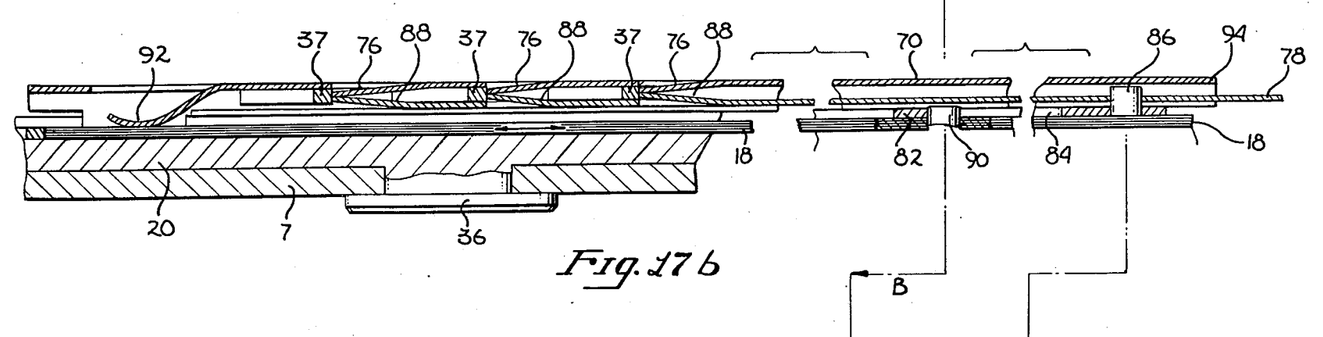
Figure 17C:
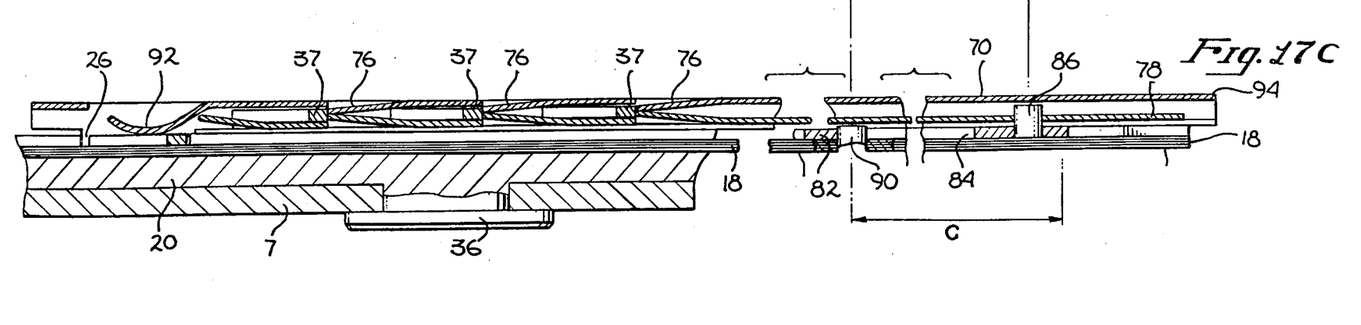

The operation of parallel clip magazine 70 can be best understood from the sequence illustrated in FIGS. 17a, 17b and 17c. In FIG. 17a parallel clip magazine 70 is shown coupled to main body 20. Disposed within parallel clip magazine 70 are leaf springs 76 extending inwardly from housing 94, clip loading blade 78 with inwardly extending leaf springs 88, and lost motion link 82. Adjacent lost motion link 82 is the clip feed blade 18, of applying device 2, which has a feed blade pin 90 attached thereto. In FIG. 17a clip feed blade 18 is in its fully retracted position so that a hemostatic clip 37 is located in recess 26 of main body 20. Hemostatic clip 37 is held in recess 26 by clip guide spring 92. Disposed within parallel clip magazine 70 are a plurality of hemostatic clips 37 which will be sequentially moved into recess 26 by the urging of leaf springs 88 coupled to clip loading blade 78. It can be seen in FIG. 17a that feed blade pin 90 is located in the extreme right hand portion of slot 84 in lost motion link 82 and that clip loading blade 78 is coupled to lost motion link 82 by lost motion link pin 86.

In FIG. 17b it can be seen that clip feed blade 18, which is coupled to upper finger loop 4, has been moved forward so that the clip 37 which was in recess 26 has been moved along its path toward the jaw portions. Correspondingly, feed blade pin 90 has freely moved the length of slot 84 in lost motion link 82, the distance A, so that neither lost motion link 82 nor clip loading blade 78 has had a forward movement. Thus, during the initial portion of the loading sequence of clip magazine 70, hemostatic clips 37 disposed within the magazine 70 have not moved, while the clip 37 which was located in the recess 26 has been moved toward the device jaws.

However, it can be seen in FIG. 17c that further forward movement of clip feed blade 18 caused by the forward movement of upper finger loop 4 has resulted in a forward movement of lost motion link 82 because pin 90 which was abutting the forward most portion of slot 84 in lost motion link 82, has moved a distance B. Thus, this subsequent forward movement of clip feed blade 18 has resulted in forward movement of lost motion link 82 and corresponding forward movement of pin 86. Forward movement of lost motion link pin 86, in turn, has caused forward movement of clip loading blade 78 and its associated leaf springs 88. Thus, the total forward movement of pin 90 a distance C has resulted in hemostatic clips 37 being moved forward and ultimately the forward most hemostatic clip 37 being guided onto the upper surface of clip feed blade 18, above recess 26 by clip spring 92. When clip feed blade 18 is returned to its static position by the return of upper finger loop 4, clip 37 will drop into recess 26 so that it will be ready to be fed to the jaw portions as illustrated in FIG. 17a.

During the later stages of the return movement of feed blade 18, clip loading blade 78 will also undergo a rearward movement. During this rearward movement of loading blade 78, leaf springs 88 will abut a clip 37 and bend outward sufficiently so that the blade 78 is not impeded. When the blade leaf springs 88 have cleared the clips 37, they will return to their inward biased position. Clips 37 are prevented from undergoing a rearward movement by the protrusion of leaf springs 76 in housing 94. That is, the bail portions of clips 37 abut the leading edge of leaf springs 76 and are prevented from moving rearward. On the other hand, forward movement of clips 37 is accomplished by the abutment of the leading edge of leaf springs 88 with the bail portion of clips 37. As springs 88 move forward due to the movement of blade 78, clips 37 bend housing leaf springs 76 outward until they have passed the protruding portions of the springs 76. In this manner, one complete forward movement of upper finger loop 4 will cause each clip 37 to progress to the next location just ahead of the next succeeding housing spring 76.

The proper alignment of both leaf springs 76 and 88 in their relationship to clips 37 is accomplished by the location of rear stop pin 16 and forward stop means 21. The rear stop pin 16 is positioned so that abutment of upper finger loop member 5 with pin 16 results in sufficient movement of clip loading blade 78 so that loading blade leaf springs 88 stop slightly behind each adjacent clip 37. This positioning of pin 16 ensures that each leaf spring 88 will be able to move the adajacent clip 37 forward. The forward stop means 21, on the other hand, is positioned so that abutment of upper finger loop member 5 results in sufficient forward movement of leaf springs 88 so that each clip 37 is placed just beyond the rearward adjacent leaf spring 76. Thus, the prevention of rearward movement of clips 37 is ensured since each leaf spring 76 is always behind the forward adjacent clip 37.

There has been described herein a new and novel clip applying device which has special utility for applying hemostatic clips to blood vessels and the like. However, it is to be understood that various alternate embodiments using the principles of the present invention may be readily incorporated. Thus, while specific embodiments of the present invention have been disclosed and described in detail herein, it will be understood by those skilled in the art that various changes in form and detail may be made therein without departing from the spirit and scope of the invention.

We claim:

1. A clip magazine adapted to associate with a surgical applying device having a main body, clip deforming means for receiving and deforming clips, and clip feed means for feeding clips from the magazine to the clip deforming means, said magazine comprising:

(i) a housing wherein a plurality of clips are stored aligned in a plane parallel to the main body, said housing having a sidewall oriented generally parallel to the clips, and a plurality of inwardly biased flexible members associated with the housing and adapted to engage the clips and thereby prevent substantial rearward movement of the clips; and (ii) clip loading means, carried within the housing, for urging the clips through the housing to the clip feed means, said loading means including a reciprocating loading blade slideably carried within the housing, said loading blade having a plurality of inwardly biased flexible members adapted to engage the clips in the magazine, wherein a forward movement of the loading blade engages the blade flexible members with the clips to advance the clips in unison and substantial rearward movement of the clips induced by a rearward movement of the loading blade is prevented by engagement of the clips with the housing flexible members; and (iii) coupling means engaging the housing and the clip applying device for coupling the housing sidewall to said clip applying device.

2. The magazine of claim 1 wherein the coupling means includes at least one spring clip adapted to snap over the magazine housing and to the main body of the device.

3. The magazine of claim 1 further comprising:
lost motion means for coupling the clip feed blade to the clip loading blade wherein a relatively long reciprocating motion of the clip feed blade causes in a short reciprocating motion of the loading blade.

4. The magazine of claim 3 wherein said lost motion means includes a slot associated with one of said feed blade and loading blade, a pin coupled to the other of said feed blade and loading blade, said pin being disposed within the slot and engaging alternate ends of the slot in accordance with the reciprocating motion of the clip feed blade.

5. The magazine of claim 1 wherein said housing members comprise a plurality of inwardly biased leaf springs whereby said loading blade sequentialy moves said clips forward through said housing while said leaf springs prevent rearward movement of said clips.

6. The magazine of claim 5 wherein said loading blade members comprise a plurality of leaf springs disposed thereon, said leaf springs in substantially opposed relationship with said leaf springs of said housing, said leaf springs of said housing and said leaf springs of said loading blade having a "V" shaped leading edge so as to engage the correspondingly shaped portion of said clips.

7. The magazine of claim 6 wherein said loading blade further includes a forward stop means coupled thereto for stopping the forward movement of the loading blade at a position which results in each clip being placed just beyond the rearward adjacent housing leaf spring at the end of forward movement of said loading blade so as to assure that said leaf springs of said housing engage said clips and prevent their rearward movement.

8. The magazine of claim 1 further including a lost motion link means adapted to associate with a feed means of a clip applying device, said link means coupled to said loading blade wherein initial forward movement of said feed means of said clip applying device does not result in forward movement of said loading blade while additional forward movement of said feed means of said clip applying device results in forward movement of said loading blade.

9. The magazine of claim 8 wherein said housing further includes a guide spring means coupled thereto, said guide spring means adapted to urge said clips from said housing into a clip applying device.

* * * * *